(12) United States Patent
Allam

(10) Patent No.: US 8,772,360 B2
(45) Date of Patent: Jul. 8, 2014

(54) GENERATING METHANOL USING ULTRAPURE, HIGH PRESSURE HYDROGEN

(75) Inventor: Rodney J. Allam, Chippenham (GB)

(73) Assignee: GTLpetrol LLC, New York, NY (US)

( * ) Notice: Subject to any disclaimer, the term of this patent is extended or adjusted under 35 U.S.C. 154(b) by 267 days.

(21) Appl. No.: 13/115,780

(22) Filed: May 25, 2011

(65) Prior Publication Data

US 2011/0294907 A1 Dec. 1, 2011

Related U.S. Application Data

(60) Provisional application No. 61/348,027, filed on May 25, 2010.

(51) Int. Cl.
*C07C 27/00* (2006.01)

(52) U.S. Cl.
USPC ........... 518/700; 518/702; 518/703; 518/704; 518/705

(58) Field of Classification Search
USPC ......................................... 518/700, 702–705
See application file for complete search history.

(56) References Cited

U.S. PATENT DOCUMENTS

| 4,631,915 A | 12/1986 | Frewer | |
|---|---|---|---|
| 6,669,744 B2 | 12/2003 | Allam | |
| 2003/0065042 A1 | 4/2003 | Shaw | |
| 2006/0074132 A1* | 4/2006 | Allam et al. | 518/702 |
| 2006/0128818 A1* | 6/2006 | Wang et al. | 518/702 |
| 2008/0081844 A1 | 4/2008 | Shires | |
| 2010/0047160 A1 | 2/2010 | Allam | |

OTHER PUBLICATIONS

International Search Report and Written Opinion of the International Searching Authority issued in International Application No. PCT/US2011/037948, mailed Sep. 19, 2011, 13 pages.
International Preliminary Report on Patentability issued in International Application No. PCT/US2011/037948, Nov. 27, 2012, 8 pages.
Australian Patent Examination Report No. 1, issued in Application No. 2011258329, mailed Aug. 5, 2013; 3 pages.

* cited by examiner

*Primary Examiner* — Jafar Parsa
(74) *Attorney, Agent, or Firm* — Fish & Richardson P.C.

(57) ABSTRACT

In various implementations, methanol is produced using a ($CO+H_2$) containing synthesis gas produced from a combined PDX plus EHTR or a combined ATR plus EHTR at a pressure of 70 bar to 100 bar at the correct stoichiometric composition for methanol synthesis so that no feed gas compressor is required for the feed to the methanol synthesis reactor loop.

11 Claims, 5 Drawing Sheets

FIG. 3A

| lbmol/hr | 2 | 5 | 6 | 27 | 7 | 8 | 9 | 10 | 41 | 42 |
|---|---|---|---|---|---|---|---|---|---|---|
| CO | | | | 1574.2 | 1806.3 | | | | | |
| H$_2$ | | | | 2761.4 | 4559.6 | | | | | |
| CO$_2$ | | 11.2 | 4.3 | 63.6 | 351.2 | | | | | |
| H$_2$O | | | 3760.5 | 409.5 | 3371.2 | | | | | |
| CH$_4$ | | 1492.7 | 571.3 | 11.1 | 122.4 | | | | | |
| O$_2$ | 1044.2 | | 3.5 | | | | | | | |
| N$_2$+Ar | 5.3 | 9.1 | | 14.4 | 17.9 | | | | | |
| C$_2$ | | 49.8 | 19.1 | | | | | | | |
| C$_3$ | | 8.5 | 3.3 | | | | | | | |
| C$_4$ | | 1.6 | 0.6 | | | | | | | |
| C$_5$ | | 0.3 | 0.1 | | | | | | | |
| C$_6$ | | 0.6 | 0.2 | | | | | | | |
| TEMPERATURE °C | | 500 | 494 | 1446 | 600 | 340 | 201 | 40 | 330 | 500 |
| PRESSURE BAR | | 80 | 80 | 79 | 78 | 77.8 | 77.5 | 77.0 | 125 | 125 |
| FLOW lbmol/hr | | | | | | | | | | |

SAME COMPOSITION AND FLOW AS POINT 7 (columns 8, 9, 10)

BASED ON A SIEMENS SGT-300 GAS TURBINE PERFORMANCE AT ISO CONDITIONS
PURE METHANOL PRODUCTION 730 MT/DAY

FIG. 3B

| lbmol/hr | 43 | 47 | 46 | 25 | 26 | 24 | 20 | 29 | 30 | 13 | 35 | 52 |
|---|---|---|---|---|---|---|---|---|---|---|---|---|
| | | | | COMPOSITION SAME AS POINT 5 | | SAME AS POINT 7 | | | | | | |
| CO | | | | | | | | | | 1806.3 | | |
| $H_2$ | | | | | | | | | | 4559.6 | | |
| $CO_2$ | | | | | | | 254 | | | 351.2 | | |
| $H_2O$ | | 3760.5 | | | | | 595 | | | 10 | 1233.6 | 1233.6 |
| $CH_4$ | | | | | | | | | | 122.4 | | |
| $O_2$ | | | | | | | 1126.2 | | | | | |
| $N_2$ + Ar | | | | | | | 5333.2 | | | 17.9 | | |
| $C_2$ | | | | | | | | | | | | |
| $C_3$ | | | | | | | | | | | | |
| $C_4$ | | | | | | | | | | | | |
| $C_5$ | | | | | | | | | | | | |
| $C_6$ | | | | | | | | | | | | |
| TEMPERATURE °C | 432 | 500 | 250 | 80 | 500 | 164 | 537 | 653 | 137 | 40 | 40 | 330 |
| PRESSURE BAR | 80.5 | 80 | 25 | 82 | 80 | 77.2 | 1.08 | 1.06 | 1.02 | 77.0 | 6.9 | 6.9 |
| FLOW lbmol/hr | | | 244.1 | 2341.8 | 602.3 | | | | | | | |

BASED ON A SIEMENS SGT-300 GAS TURBINE PERFORMANCE AT ISO CONDITIONS

PURE METHANOL PRODUCTION 730 MT/DAY

GENERATING METHANOL USING ULTRAPURE, HIGH PRESSURE HYDROGEN

CLAIM OF PRIORITY

This application claims priority under 35 U.S.C. §119 to U.S. Provisional Application No. 61/348,027, filed May 25, 2010, the entire disclosure of which is incorporated herein by reference.

TECHNICAL FIELD

The present invention relates to producing methanol and, more particularly, to producing methanol using a carbon monoxide plus hydrogen ($CO+H_2$) synthesis gas mixture produced at a pressure above the pressure required in the methanol synthesis reactor without any subsequent compression.

BACKGROUND

Methanol, also known as methyl alcohol, wood alcohol, wood naphtha or wood spirits, is a simple alcohol, with the formula $CH_3OH$, that is a light volatile flammable poisonous liquid alcohol. Methanol has extensive uses in the production of a range of chemicals including ethylene glycol, acetic acid, vinyl acetate. Methanol may also be used for producing biodiesel via trans-esterification reaction. Methanol is produced naturally in the anaerobic metabolism of many varieties of bacteria and is ubiquitous in the environment. Methanol is produced commercially by combining CO and $CO_2$ with hydrogen in a catalytic reactor operating at pressures typically in the range 70 to 100 bar and temperatures in the range 250° C. to 300° C. Commonly used methods of producing the $CO+H_2$ synthesis gas from natural gas include steam/hydrocarbon catalytic reforming (SMR), catalytic auto-thermal reforming (ATR), partial oxidation (POX), and combinations of the forgoing. A combination of the ATR and a convectively heated SMR is the basis of the well known Leading Concept Ammonia Process. The synthesis gas generation system is described in a paper "A Methanol Technology for the 20$^{th}$ Century" by R Kirkpatrick and T Fitzpatrick presented at the World Methanol Conference San Diego November 1999. In each case except POX, the synthesis gas from the optimum generation pressure is compressed to the higher pressure required by the methanol reactor system. POX can produce syngas at pressures in the range 70 to 100 bar but it is not an economic method in isolation since it produces synthesis gas at a very high temperature of 1300° C. to 1400° C. and there is a large specific oxygen requirement.

SUMMARY

In various implementations, methanol is produced using $CO+H_2+CO_2$ synthesis gas produced using the basic combination of POX+EHTR (Enhanced Heat Transfer Reformer) which can produce methanol according to the following reactions:

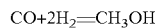

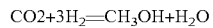

Synthesis gas can be produced at a pressure in the range 70 bar to 100 bar with a methane content which does not exceed 2% molar (dry basis). The combination of a POX+EHTR using a gas turbine may provide the power for the oxygen plant air compressors as described in U.S. Pat. Nos. 6,534,551 and 6,669,744. Providing the power the gas turbine may result in a combination of heat recovery in the synthesis gas generation system and in the circulating methanol synthesis reactor loop, which may result in optimum or otherwise increased heat recovery and may provide substantially all of the shaft power and process heat for synthesis gas generation, methanol synthesis, and methanol purification systems. The combustible effluents discharged from the methanol purification system may be incinerated at near atmospheric pressure in the gas turbine exhaust fired heater, which may produce heating for the steam and natural gas feeds to the POX+EHTR synthesis gas generation system. This highly efficient use for these combustible effluents may replace natural gas feed on an equivalent heat release basis. The combustible effluents may include at least one of a fusel oil, purge gas from the loop, or vent gas from distillation and pressure let down vessel.

In some implementations, the methanol-producing system can include a POX plus EHTR with very high steam to active carbon ratio in the EHTR reformer feed, which may produce a synthesis gas mixture leaving the waste heat boiler at temperatures from 300° C. to 400° C. and a pressure from 70 bar to 100 bar. The steam to active carbon ratio in the EHTR feed stream can typically be in the range of about 5 to 8 such as the range of about 5.5 to 6.5. To achieve a methane content in the dry syngas of less than 2% molar, the EHTR may operate at a high steam to active carbon ratio. In order to operate the EHTR in combination with a POX reactor to maximize or otherwise increase syngas output from a given total natural gas feed, the POX may be operated with a much higher than normal ratio of oxygen to natural gas. Normal operation of a POX system with oxygen gives good performance with methane content in the exit gas on a dry basis in the range 0.25% to 0.5% molar when the POX discharge temperature is in the range of 1300 to 1350° C. The POX reactor may result in an outlet temperature of between 1400° C. and 1500° C. with natural gas feed. An example uses a steam to active carbon ratio of 6.03 in the EHTR, which may have an outlet shell side temperature of about 600° C., a tube side exit temperature of about 900° C., a POX outlet temperature of about 1446° C. and a mixed shell side inlet temperature on the EHTR shell side of about 1131° C. The waste heat boiler outlet syngas temperature may be about 320° C. and the syngas pressure may be about 77 bar. The syngas may contain approximately the following components: (1) CO lb mols 1806.31; and (2) $CO_2$ lb mols 351.18. For stoichiometry in the production of methanol, these components may include about 3×351.18+ 2×1806.31=4666.16 lb mols $H_2$. The actual content may be about 4559.56 lb mols, which may allow for the small excess of $CO+CO_2$.

The syngas leaving the waste heat boiler may be cooled in a first heat exchanger against condensate and then against deoxygenated boiler feed-water. The cooled syngas may then be cooled against an ambient cooling system such as cooling water to a temperature at which the water content is largely in the liquid phase. The water may be separated as it adversely effects the equilibrium composition and conversion of syngas to methanol per pass of the syngas through the methanol reactor. The pressure of the steam generated in the waste heat boiler may be considerably higher than the steam pressure used for the feed to the EHTR. The saturated steam produced in the waste heat boiler may be superheated in the gas turbine exhaust fired heater and may be reduced in pressure for the EHTR to produce excess power in a pass-out steam turbine. The pass-out steam may be further superheated in the heater to a temperature in the range 450° C. to 550° C. before or after mixing with the feed to the methanol synthesis gas loop at a pressure substantially equal to a pressure for the direct feed to the methanol loop with substantially no additional gas compression. In addition, the water content can typically be in the range of about 0.1 to 0.15% molar, and the methane content may be below 2%. This combination of properties may result in an ideal syngas feed to the methanol loop. All flammable effluents from the methanol loop may be combusted efficiently in the gas turbine fired heater. Using a gas turbine drive for the oxygen plant air compressor drive system may result in the methanol plant not using stand-by steam boilers to generate the steam for the compressor drive systems, which are generally steam turbine driven in existing methanol plants. The proposed POX-EHTR combination with the features shown is an efficient method at present developed for the production of syngas for methanol synthesis.

Operation of the methanol loop may be entirely from this point onwards. The heat generated in the methanol synthesis reaction may be conventionally recovered and partly or wholly used to provide the heat for operation of the methanol purification distillation system. Excess steam at medium to low pressure may be used to produce excess power in a condensing steam turbine, which may be added to the passout steam turbine. The details of one or more implementations are set forth in the accompanying drawings and the description below.

DESCRIPTION OF DRAWINGS

FIG. 3 illustrates stream compositions flows temperatures and pressures for an example of a feed stream being processed by the system illustrated in FIG. 2.

Like reference symbols in the various drawings indicate like elements.

DETAILED DESCRIPTION

In various implementations, a feed stream can be processed to produce a synthesis gas for methanol production which may have one or more of the following characteristics: a stoichiometric ratio of $H_2$ to $(CO+CO_2)$ for methanol production; a production pressure in the range of about 70 bar to 100 bar which may not include further compression to feed the synthesis gas directly into the methanol reactor loop; a synthesis gas with less than about 2% molar methane content; a synthesis gas with less than about 0.2% molar water content; combustible effluents from the methanol production and a purification system that returns to them to synthesis gas production process for combustion; returning excess steam produced by the methanol production and purification process to the synthesis gas production process where it can be used to produce power; and/or others. The processed feed streams may include a variety of feed streams that include methane, such as natural gas, hydrocarbon fuels, methane rich gases such as coal-bed methane or biogas (e.g., stream produced from the anaerobic decay of matter). The feed streams may include liquid hydrocarbon streams.

The following description provides examples of operating temperatures, pressures and concentrations in connection with describing the methanol systems and operations. These values are for illustration purposes only and the invention may use some, all or none of these values without departing from the scope of this disclosure.

Figure 1:
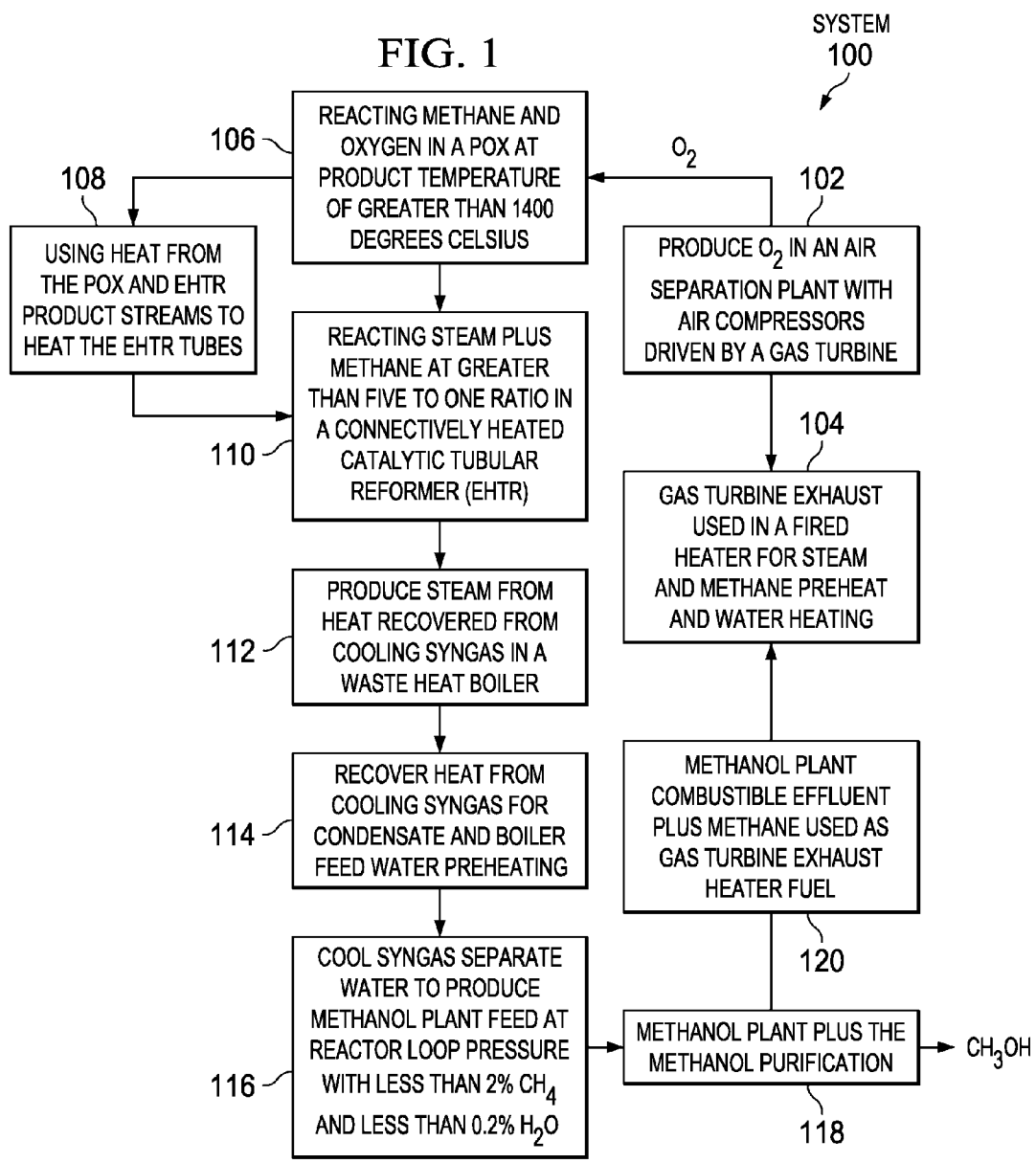
FIG. 1 illustrates an example system for the production of synthesis gas for a methanol plant.

FIG. 1 is a flow chart illustrating an method 100 for generating methanol in accordance with some implementations of the present disclosure. Generally, the method 100 describes an example technique for using purge gas from a methanol loop as a feed stream to a gas turbine. Method 100 contemplates using any appropriate combination and arrangement of logical elements implementing some or all of the described functionality.

Method 100 begins at step 102 where oxygen is produced in an air separation plant with air compressors driven by a gas turbine. At step 104, exhaust from the gas turbine is used in a heat exchanger for heating steam, water, and methane preheat. Methane and oxygen are reacted in a POX at a temperature greater than about 1400° C. at step 106. Next, at step 108, heat from the product streams of the POX and EHTR are used to heat the EHTR tubes. In connection with recycling the heat, steam and methane are reacted at ratio greater than about 5 to 1 in a convectively heated catalytic tubular reformer (e.g., EHTR) at step 110. Next, at step 112, steam is produced using heat recovered from cooling syngas in a waste heat boiler. In addition, heat is recovered from cooling syngas for condensate and boiler feed-water preheating at step 114. At step 116, water is separated from the cooled syngas to produce methanol plant feed at reaction loop pressure with less than about 2% $CH_4$ and less than about 0.2% $H_2O$, Next, at step 118, the stream is passed to the methanol plant and methanol purification. Methanol plant combustible effluent plus methane used as gas turbine exhaust heater fuel at step 120.

Figure 2:
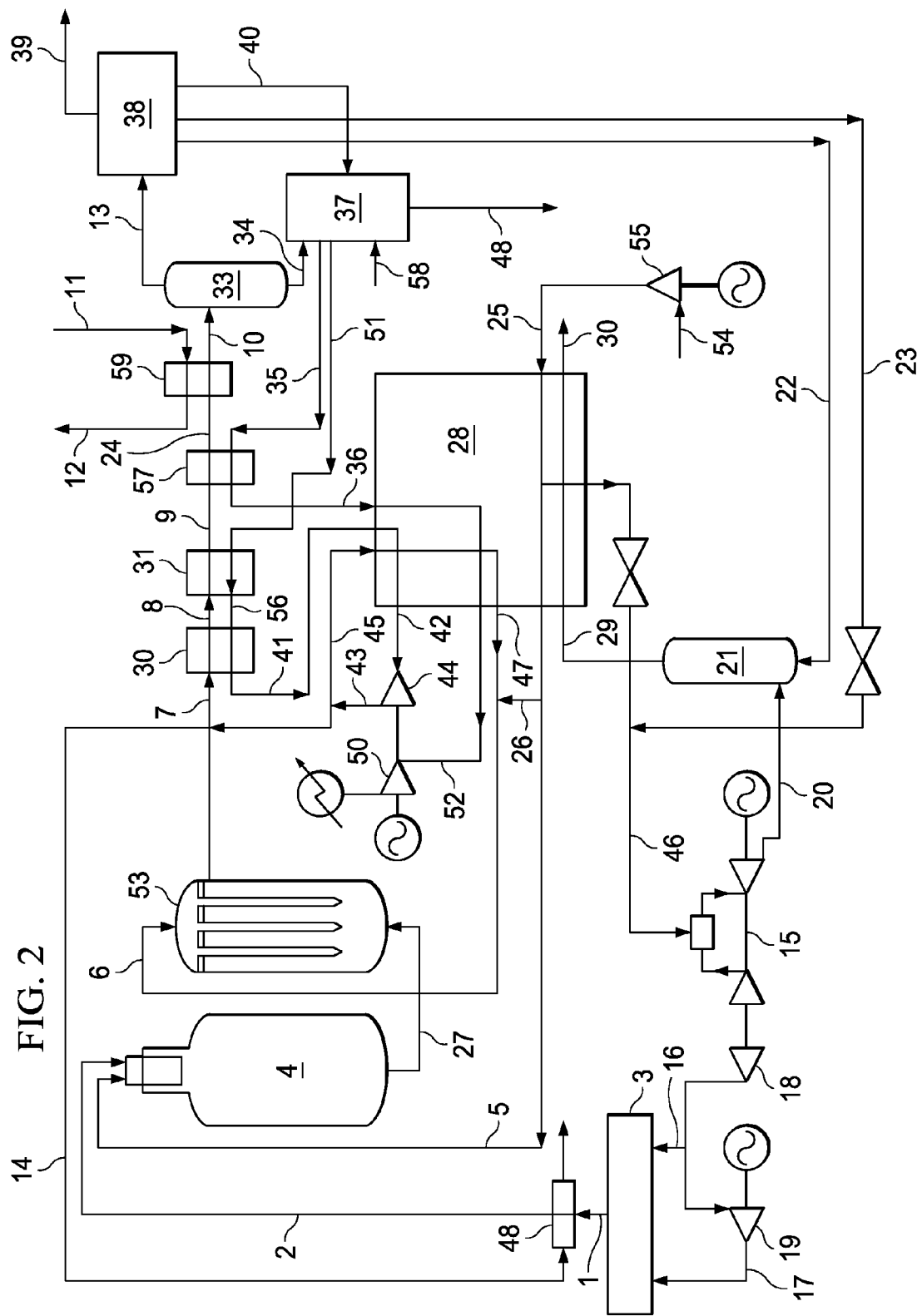
FIG. 2 illustrates a detailed flow scheme for the production of synthesis gas for a methanol plant.

FIG. 2 is a detailed flow scheme showing the syngas, methanol, energy system and water treatment system in accordance with some implementations of the present disclosure. Pre-heated feed streams 5 and 6 may be introduced into synthesis gas generation systems 4 and 53. For example, a feed stream, such as natural gas, may be introduced to a POX/EHTR synthesis gas generation system, as illustrated, that includes a Partial Oxidation Reactor (POX) combined with a Gas Heated Catalytic Reformer (EHTR), in which the combined POX product gas and the product gas from the EHTR are used to provide the total or at least a substantial portion of the heat requirement of the convectively heated EHTR. As illustrated, a compressed heated oxygen stream 2 may be generated in a pumped liquid oxygen cryogenic Air Separation Unit (ASU) 3. The oxygen stream 2 may be preheated (e.g., by heat from condensing steam stream 14. and provided to a POX with a natural gas feed stream 5. A gas turbine 15 may drive an air compressor 18, which may provide the feed air stream 16 at about 5.8 bar to the ASU 3. A portion of the feed air stream 16 is further compressed to, for example, about 70 bar in a booster compressor 19. The booster compressor 19 may be driven by an electric motor which derives its electric power from a generator coupled to the gas turbine 15. A portion of the feed stream (e.g., natural gas) 46 may be provided to the gas turbine 15 as fuel. Stream 46 may comprise natural gas mixed with methanol loop purge gas stream 23 derived from the methanol plant and suitably reduced in pressure. It is preheated to a temperature of, for example, about 250° C. The gas turbine exhaust 20 may be at, for example, approximately 537° C. The gas turbine exhaust 20, which may include oxygen, may be provided as the combustion air stream for the fired heater burner 21 which uses a combination of 2 fuel streams. Firstly the low pressure gaseous combustible effluent from the methanol plant and secondly a combustible liquid fuel stream 22 from the methanol plant. The combustion product 29 from the burner 21 enters the convection section of the fired heater 28. The cooled exhaust gas 30 is discharged from the heater to the atmosphere at a temperature of, for example, about 137° C.

The natural gas feed stream 54 at 40 bar is compressed to 82 bar in compressor 55 and enters the heater as stream 25 at 80° C. This stream is heated to 500° C. and divided into stream 5, the POX feed and stream 26 which may be mixed with the superheated steam stream 47 at about 500° C. The combined stream 6 is the feed to the catalyst filled tubes of the EHTR. A sidestream of natural gas preheated to 320° C. is taken off to form part of the gas turbine fuel stream 46.

In the POX 4, the natural gas stream 5 may be partially oxidized with oxygen stream 2 to produce synthesis gas stream 27 (e.g., a stream that includes hydrogen and carbon monoxide). The synthesis gas stream 27 may include unreacted feed from the natural gas stream 5 and/or byproducts such as carbon dioxide, methane, nitrogen, argon, oxygen, and water vapor. The synthesis gas stream 27 is at a temperature of 1446° C. and enters the shell side of the EHTR reactor 53. This temperature may be much higher than the normal exit temperature of a natural gas fed POX reactor which would be about 1345° C. The excess heat present in the POX exit gas due to the higher temperature may allow the EHTR to be operated at a pressure of 80 bar with a steam to active carbon ratio of 6.03 so that the total outlet flow from the POX plus the EHTR stream 7 may have a methane concentration of 1.8% molar (dry basis).

In some implementations, a stream 6 including a mixture of natural gas and/or steam (e.g., at approximately 500° C.) may also be fed into the EHTR. The mixture of natural gas and steam may flow downwards through the catalyst in the EHTR (e.g., catalyst filled vertical open ended tubes) and may exit the EHTR tubes as a mixture of hydrogen and carbon monoxide plus some carbon dioxide, methane, nitrogen, argon and water vapor. This gas may exit at approximately 900° C. This gas stream may also mix with the product gas stream 27 from the POX. The combined stream (e.g., gas exiting the catalyst tubes mixed with the product stream from the POX) may flow upwards through the shell side of the EHTR and/or may provide the heat required for the steam/hydrocarbon reforming reactions. The product gas stream 7 may exit the EHTR at approximately 600° C. The product gas stream 7 may include synthesis gas and may be cooled to produce a cooled stream 8. The product gas stream 7 may be cooled in a waste heat boiler from 600° C. to 340° C. producing steam stream 41 from a preheated boiler feedwater stream 56. The steam stream 41 at 330° C. and 125 bar exiting the waste heat boiler 30 is superheated to 500° C. as it passes though the fired heater 28 exiting as stream 42. This stream enters a pass-out turbine 44 where its pressure is reduced to 80.5 bar at a temperature of 432° C. The exit stream divides. Stream 14 is condensed in the oxygen heater 48, while the remainder, stream 45, enters the fired heater 28 and is heated to, for example, 500° C. Stream 47 then mixes with the preheated natural gas stream 26, becoming the EHTR tube side feed stream 6. The syngas stream 8 is cooled in heat exchanger 31 to 201° C. while heating the boiler feed water stream 51 to 310° C. There may be a large quantity of uncondensed steam present in stream 9. The syngas is cooled to, for example, 164° C. in heat exchanger 57 which may be used to preheat and evaporate a boiler feed water stream 35 at, for example, 6.9 bar which leaves as stream 36 to enter the fired heater 28 where its temperature is raised to, for example, 330° C. Stream 52 produces power in the condensing steam turbine 50. The condensed water stream 58 together with all, substantially all or other water streams enter the water purification and treatment system 37. A treated water stream 48 may be discharged from the system. The syngas stream 24 is then cooled to 40° C. against heating cooling water streams 11 to 12 in heat exchanger 59. Condensed water is separated in 33 and the syngas stream 13 enters the methanol synthesis loop and purification system 38. Substantially pure methanol may be produced at a rate of, for example, about 730 metric tons/day as stream 39. The syngas stream 13 may be reheated in 59 to 150° C. before entering the methanol loop to increase the excess steam production from the methanol synthesis and purification system.

In general, the feed stream 5 may undergo partial oxidation (eqn 1) in a POX reactor, for example. In addition, some total oxidation (eqn 2) may occur, and there may be a shift reaction (eqn 4). The reactions may include:

$$CH_4 + \tfrac{1}{2}O_2 \rightarrow CO + 2H_2 \quad (1)$$

$$CH_4 + 2O_2 \rightarrow CO_2 + 2H_2O \quad (2)$$

The product synthesis gas from the POX reactions produces a very high temperature gas mixture that may be used to provide part of the endothermic heat of reaction for steam/hydrocarbon reforming in a secondary downstream convectively heated catalytic reformer (EHTR). The remaining part of the heat requirement is provided by mixing the product gas from the EHTR tubes at 900° C. with the product gas from the POX at 1446° C. prior to the total gas stream being used to heat the GHR. The steam reforming reactions may include:

$$CH_4 + H_2O \rightarrow CO + 3H_2 \quad (3)$$

$$CO + H_2O \rightarrow CO_2 + H_2 \quad (4)$$

The synthesis gas stream 7 may include hydrogen and carbon monoxide. The synthesis gas stream 7 may also include methane, water vapour, carbon dioxide, argon, and/or nitrogen. The relative concentrations of carbon monoxide and hydrogen may depend, for example, on the hydrocarbon feed composition (e.g., methane is only used in these equations for simplicity, but other components may be present in the feed and be oxidized and/or reformed), pressure, POX outlet temperature. EHTR catalyst tube outlet temperature, the feed temperature of oxygen, natural gas and steam to POX and EHTR, the steam to active carbon ratio in the feed to the EHTR and the shell side outlet temperature from the EHTR. The oxygen purity can be in the range 90 to near 100% by volume $O_2$ and, more particularly, can be in the range 95% to 99.5% $O_2$ by volume. The ideal oxygen purity is in the range 99% to 99.9% molar to minimize methanol loop purge gas loss.

In some implementations, methanol is produced directly from the synthesis gas generation system at high purity (e.g., 95% or greater). Operation of the proposed syngas generation system may be carried out at pressures in the range 70 bar to 100 bar which may allow the produced synthesis gas to enter the circulating methanol synthesis reactor loop independent or without using a feed gas compressor. Reactions 1 to 3 are adversely affected by higher pressures, while reaction 4 is independent of pressure. Reactions 1 and 2 may compensate for higher pressure by the increase in reaction temperature, which may be achieved through a slight increase in the oxygen to hydrocarbon ratio in the POX feed. The increase in the oxygen to hydrocarbon ratio and the increase in temperature will not cause significant problems in the design of the equipment.

In order for the EHTR system to operate as a steam/hydrocarbon reforming reactor at high pressures above 70 bar, the system 100 may use a very high steam to active carbon ratio in the feed to the GHR in order to control the methane concentration in the synthesis gas product 7. This may be in the range 5 to 8 and such as the range 5.5 to 6.5. The actual steam to active carbon ratio in the feed to the GHR depends on the pressure and the GHR catalyst tube outlet temperature. The ratio may be chosen to limit the ratio of $CH_4$ to ($H_2$+CO) in the synthesis gas product leaving the GHR tubes to at least about 5% such as in the range 5% to 10% (molar). This may result in a methane concentration in the syngas product stream 7 below 2% molar (dry basis). In order to compensate for the extra heat load on the EHTR, the POX outlet temperature may be higher than a normal figure of about 1340° C. The POX outlet temperature may be raised by increasing the oxygen to hydrocarbon ratio in the POX feed so that the POX outlet temperature is above, for example, 1400° C. such as in the range 1425° C. to 1500° C. When using an ATR, the outlet temperature may be in general below 1050° C. and in this case the ratio of synthesis gas from the ATR to that from the EHTR may be increased.

In order for the EHTR system to operate as a steam/hydrocarbon reforming reactor at high pressures (e.g., above 70 bar), a very high steam to active carbon ratio in the feed may be used. Thus, for the production of synthesis gas, a higher methane content in the outlet gas from the EHTR may be produced. However, the outlet gas stream from the POX may not have a higher methane content because it is operating at a higher discharge temperature. Since about 70% of the syngas is produced from the POX reactor and only about 30% from the EHTR, it is possible to tolerate a much larger $CH_4$ content in the GHR outlet gas than from, for example, a stand-alone steam/natural gas reformer. Although it is not possible to increase the outlet temperature from the ATR, the outlet temperature of greater than 1000° C. means that the $CH_4$ content may be less than 1% in the pressure range 70 bar to 100 bar, so an increase caused by the desire to increase the reaction pressure may not have a significant effect. It is however preferably to use the POX/EHTR combination as this gives lower methane concentration in the syngas feed to the methanol loop and thus minimizes or otherwise reduce loop purge gas loss. A further characteristic of the EHTR design used in this process is the fact that the EHTR catalyst filled tubes are mounted in a vertical bundle with an inlet tube sheet at the top colder end, and with the bottom hot outlet ends open, so that the tubes are free to expand downwards when heated to operating outlet temperatures, which may be in the range 800° C. to 900° C. This means that the pressure difference between the inside and outside of the GHR tubes, when operating at design conditions, may be small. The sum of the pressure drop in the catalyst filled tube plus the shell side pressure drop may have a maximum value at the cold upper end of the GHR tubes and approximately zero at the bottom hot end of the tubes. The GHR may operate at any pressure up to an economic limitation caused by the pressure vessel design and any pressure constraint in the gas purification system chosen caused by the progressively higher gas pressure. In some implementations, this operation can be different from a steam/natural gas reformer, where the furnace operates at near atmospheric pressure, and the strength of the tubes imposes a pressure limitation on the synthesis gas pressure which is generally below 35 to 40 atm. These features may produce the $CO+CO_2+H_2$ feed gas for a low pressure methanol synthesis system operating at a loop pressure in the range 70 to 100 bar.

The benefits of this disclosure are that the overall efficiency of the methanol plant may be increased and cost may be reduced by operating the synthesis gas system at high pressure, which may reduce equipment size and cost. In addition, the methanol system substantially eliminate the conventional synthesis gas compression system and introduces hot feed gas into the loop and may allow extra by-product power production.

FIG. 3 illustrates a chart 300 including operating conditions for the methanol system of FIG. 1. Based on the conditions defined in chart 300 and the flow-sheet in FIG. 2, the system may include one or more of the following performance characteristics: methanol production at about 730 metric ton/day; total natural gas feed at about 828.26 million BTU/day (LHV basis); specific heat rate at about 26.43 million BTU (LHV basis) per metric ton methanol; oxygen flow at about 364 metric tons/day at 99.5% molar purity 85 bar; and/or others. In some implementations, the chart 300 may be based on the use of a Siemens SGT-300 Gas Turbine. Having a notional efficiency of about 55% (LHV basis) for about 3.9 Mw export power, the thermal efficiency of methanol production may be about 71.5% (LHV basis).

Figure 4:
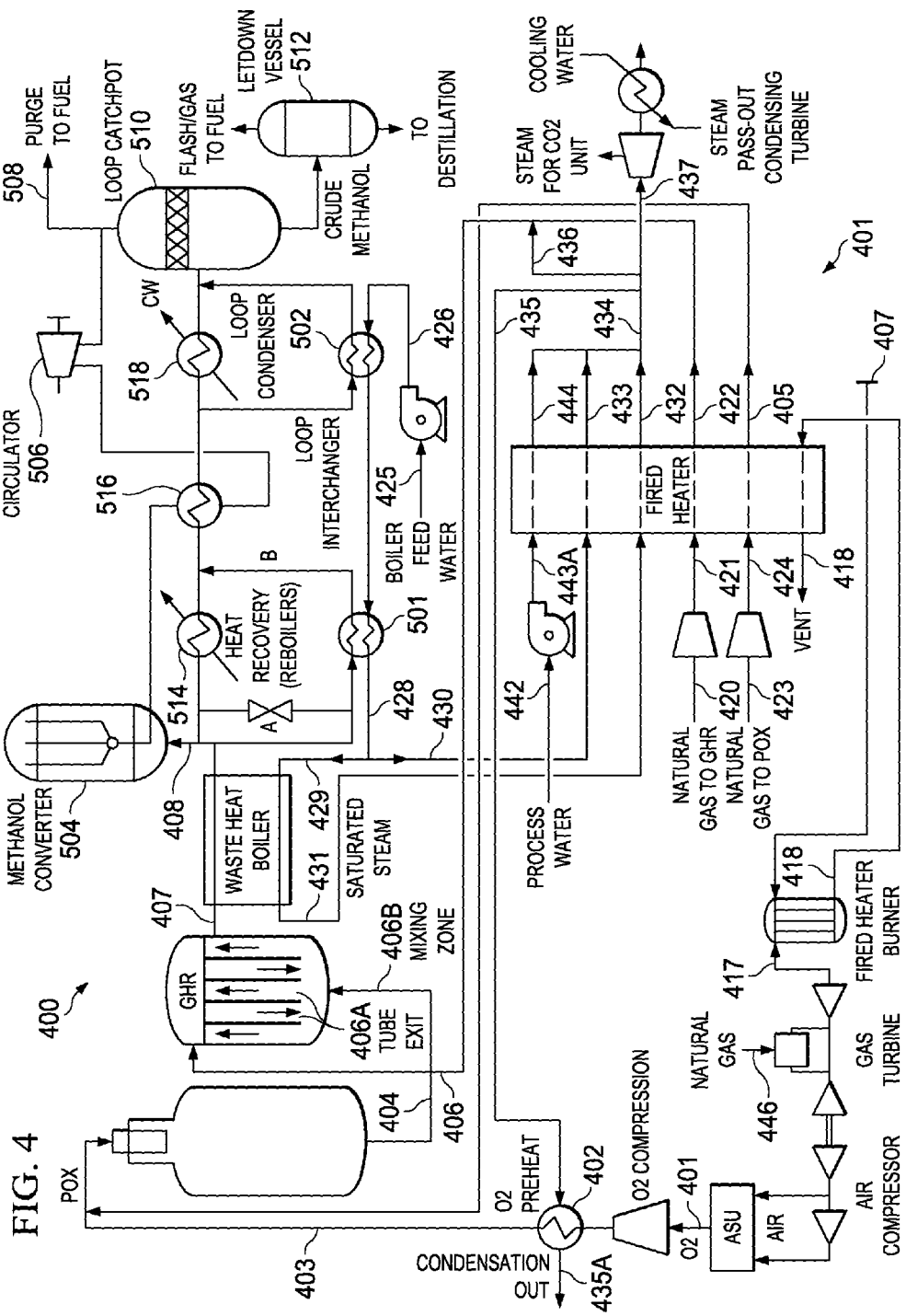
FIG. 4 illustrates another example system for the production of synthesis gas for a methanol plant.

FIG. 4 illustrates another example of a methanol system 400 that integrates the syngas system with the heat exchange. As previously stated, a feed stream is, in various implementations, processed to produce high pressure (e.g., greater than approximately 70 bars) syngas streams comprising mixtures of $CO+CO_2+H_2$ suitable in composition for the production of methanol in, for example, an acatalytic process. The processed feed streams may include a variety of feed streams that include methane, such as natural gas, hydrocarbon fuels, methane rich gases such as coalbed methane or biogas (e.g., stream produced from the anaerobic decay of matter). The feed streams may include liquid hydrocarbon streams. A preheated feed stream 405 may be introduced into synthesis gas generation systems 404 and 407. For example, a feed stream, such as natural gas, may be introduced to a POX/EHTR synthesis gas generation system, as illustrated, that includes a Partial Oxidation Reactor (POX) combined with a Gas Heated Catalytic Reformer (EHTR), in which the combined POX product gas and the product gas from the EHTR are used to provide the total or at least a substantial portion of the heat requirement of the EHTR. As another example, the feed stream may be fed into an ATR/EHTR combined synthesis gas generation system that includes an Autothermal Reformer (ATR) combined with a EHTR, in which the combined ATR product gas and gas from the EHTR are used to provide the total or at least a substantial portion of the heat requirement of the EHTR. As illustrated, a compressed oxygen stream 402 may be generated in a pumped liquid oxygen cryogenic Air Separation Unit (ASU). The oxygen stream 402 may be preheated (e.g., by heat from steam heated by fuel 438 combusted in a fired heater burner), and provided to a POX with a natural gas feed stream 405. The natural gas feed stream 405 may be preheated (e.g., by heat generated by a fuel 438 and/or natural gas 447, such as natural gas from the feed stream, combusted in a fired heater burner).

In the POX, the natural gas stream 405 may be partially oxidized to produce synthesis gas stream 404 (e.g., a stream that includes hydrogen and carbon monoxide). The synthesis gas stream 404 may include unreacted feed from the natural gas stream 405 and/or byproducts such as carbon dioxide, methane, nitrogen, oxygen, and water vapor. The synthesis gas stream 404 may enter the shell side of the EHTR 407.

In some implementations, a stream 406 including a mixture of natural gas and/or steam (e.g., at approximately 550° C.) may also be fed into the EHTR. The stream 406 may be preheated (e.g., by heat generated by fuel 438 combusted in a fired heater burner). The mixture of natural gas and steam may flow downwards through the catalyst in the EHTR (e.g., catalyst filled vertical open ended tubes) and may exit the EHTR as a mixture of hydrogen and carbon dioxide plus some carbon monoxide, nitrogen, argon and water vapor. This gas may exit at approximately 900° C. This gas stream may also mix with the product gas stream 404 from the POX. The combined stream (e.g., gas exiting the catalyst tubes mixed with the product stream from the POX) may flow upwards through the shell side of the EHTR and/or may provide the heat required for the steam/hydrocarbon reforming reactions. The product gas stream 407 may exit the GHR at approximately 600° C. The product gas stream 407 may include synthesis gas and may be cooled to produce a cooled stream 408. The product gas stream 407 may be cooled in a waste heat boiler producing steam stream 431 from a preheated boiler feedwater stream 429. The steam stream 431 exiting the waste heat boiler may include saturated steam and may be superheated as it passes though the fired heater.

In general, the feed stream 405 may undergo partial oxidation (eqn 1) in a POX reactor, for example. In addition, some total oxidation (eqn 2) may occur, and there may be a shift reaction (eqn 3). The reactions may include:

$$CH_4 + \tfrac{1}{2}O_2 \rightarrow CO + 2H_2 \qquad (1)$$

$$CH_4 + 2O_2 \rightarrow CO_2 + 2H_2O \qquad (2)$$

The product synthesis gas from the POX reactions produces a very high temperature gas mixture that may be used to provide part of the endothermic heat of reaction for steam/hydrocarbon reforming in a secondary downstream gas-heated catalytic reformer (EHTR). The remaining part of the heat requirement is provided by mixing the product gas from the EHTR with the product gas from the POX prior to the total gas stream being used to heat the EHTR. The steam reforming reactions may include:

$$CH_4 + H_2O \rightarrow CO + 3H_2 \qquad (3)$$

$$CO + H_2O \rightarrow CO_2 + H_2 \qquad (4)$$

The synthesis gas stream 531 may include hydrogen and carbon monoxide. The synthesis gas stream 531 may also include unreacted feed components, water, carbon dioxide, argon, and/or nitrogen. The relative concentrations of carbon monoxide and hydrogen may depend, for example, on the hydrocarbon feed composition (e.g., methane is only used in these equations for simplicity, but other components may be present in the feed and be oxidized and/or reformed), pressure, and/or outlet temperature from the catalyst beds. The oxygen purity can be in the range 90 to near 100% by volume $O_2$ and, more particularly, can be in the range 95% to 99.5% $O_2$ by volume.

The objective of this process is to produce methanol directly from the synthesis gas generation system at high purity. Reactions 1 to 3 are adversely affected by higher pressures, while reaction 4 is independent of pressure. Reactions 1 and 2 may compensate for higher pressure by a relatively small increase in reaction temperature, which may be achieved through a slight increase in the oxygen to hydrocarbon ratio. The increase in the oxygen to hydrocarbon ratio and the small increase in temperature will not cause significant problems in the design of the equipment.

In order for the EHTR system to operate as a steam/hydrocarbon reforming reactor at high pressures above 60 bar, the system 100 may use a very high steam to active carbon ratio in the feed to the EHTR in order to control the methane concentration in the synthesis gas product 407. This should be above 5, and preferably in the range 5 to 10. The actual steam to active carbon ratio in the hydrocarbon feed to the GHR depends on the pressure and the EHTR catalyst tube outlet temperature. The ratio is chosen to limit the ratio of $CH_4$ to $(H_2+CO)$ in the synthesis gas product leaving the EHTR tubes to a at least about 5% and preferably in the range 5% to 10% (molar). In order to compensate for the extra heat load on the EHTR caused by the difference in temperature between the feed to the EHTR tubes and the temperature of the product stream 407 leaving the shell side, the POX outlet temperature should be higher than a normal figure of about 1340° C. The POX outlet temperature may be raised by increasing the oxygen to hydrocarbon ratio in the POX feed so that the POX outlet temperature is above 1400° C. and preferably in the range 1425° C. to 1500° C. When using an ATR, the maximum outlet temperature will be in general below 1050° C. and in this case the ratio of synthesis gas from the ATR to that from the EHTR will be increased.

In order for the EHTR system to operate as a steam/hydrocarbon reforming reactor at high pressures (e.g., above 60 bar), a very high steam to active carbon ratio in the feed may be used. Thus, for the production of synthesis gas, a higher methane content in the outlet gas from the EHTR and ATR will be produced. However, the outlet gas stream from the POX may not have a higher methane content. Since about 70% of the syngas is produced from the POX reactor and only about 30% from the GHR, it is possible to tolerate a much larger $CH_4$ content in the EHTR outlet gas than from, for example, a stand-alone steam/natural gas reformer. Although it is not possible to increase the outlet temperature from the ATR, the outlet temperature of greater than 1000° C. means that the $CH_4$ content will be less than 1%, so an increase caused by the desire to increase the reaction pressure will not have a significant effect. A further characteristic of the EHTR design used in this process is the fact that the EHTR catalyst filled tubes are mounted in a vertical bundle with an inlet tube sheet at the top colder end, and with the bottom hot outlet ends open, so that the tubes are free to expand downwards when heated to operating outlet temperatures, which will be in the range 800° C. to 900° C. This means that the pressure difference between the inside and outside of the EHTR tubes, when operating at design conditions, is quite small. The sum of the pressure drop in the catalyst filled tube plus the shell side pressure drop is a maximum value at the cold upper end of the EHTR tubes and approximately zero at the bottom hot end of the tubes. The EHTR can operate at any pressure up to an economic limitation caused by the pressure vessel design and any pressure constraint in the gas purification system chosen caused by the progressively higher gas pressure. This is quite different from a steam/natural gas reformer, where the furnace operates at near atmospheric pressure, and the strength of the tubes imposes a pressure limitation on the synthesis gas pressure which is generally below 35 to 40 atm.

The total synthesis product gas stream 407 is at a temperature in the range 600° C. to 800° C. It is passed through a heat recovery steam boiler, which receives a boiler feedwater stream 429 and produces a steam stream 31. The cooled synthesis gas stream 8 is passed through the methanol converter 104. In some implementations, the syngas stream 408 may be about 77 bars at a point immediately up-stream of the heat recovery (reboilers 514). The stream 408 may include a very large amount of steam so a parallel heat exchanger 501 to the reboilers 514 may produce heating by the boiler feedwater stream point 428. The inlet feed water stream from the pump point 426 may be preheated in an exchanger 502, which may be placed in parallel with the loop condenser 518. In addition or alternatively, the heat exchanger 502 may be placed upstream and in series with the loop condenser 518. The system 400 partially introduces the stream 408 at the exit of the methanol converter 504 and partly or wholly directly into heat exchanger 501. A water separator may be located at point B to separate water condensed from the stream 408 directly without diluting the methanol product and increasing separation costs. The boiler feed water may be heated as described above. The natural gas stream point 447 will provide the fuel required by the fired heater burner supplemented by the purge gases produced in the methanol loop and the methanol distillation system.

These features may produce the $CO+CO_2+H_2$ feed gas for a low pressure methanol synthesis system at a loop pressure in the range 50 to 100 bar and at a temperature in the range 200° C. to 400° C., which be close to the operating temperature of the methanol synthesis reactor 504.

The benefits of this invention are that it increases the overall efficiency of the methanol plant and reduces cost by operating the synthesis gas system at high pressure thus reducing equipment size and cost, that it eliminates the conventional synthesis gas cooling and compression system and that it introduces hot feed gas into the loop and allows extra by-product power production.

A gas turbine may drive an air compressor, which may provide the feed air stream to the ASU. A portion of the feed stream (e.g., natural gas) 446 may be provided to the gas turbine as fuel. The gas turbine exhaust 417 may be at approximately 450° C. The gas turbine exhaust 417, which includes oxygen, may be provided as the combustion air stream for the fired heater burner.

The fired heater may heat a first part 423 of the feed stream (e.g., natural gas) to be provided to the POX. The first part 423 may be compressed, and the compressed first part 424 may be heated by the fired heater to produce a preheated feed stream 405 that is provided to the POX. The fired heater may also heat a second part 420 of the feed stream to be provided to the EHTR. The second part 420 may be compressed, and the compressed second part 421 may be heated in the fired heater to produce a preheated feed stream 422 to be provided to the EHTR. Process water 442, together with saturated steam stream 431, may also be heated to produce multiple streams 444, 433, 432, and total superheated steam stream 434 of steam at 80 bar 500° C. for the process. The steam stream 434 splits into stream 435, used for preheating the $O_2$ feed to the POX or ATR and streams 436 and 437, stream 436, is added to stream 422 to produce the total feed gas steam 406 to the tube side of the EHTR, and stream 437, includes the remaining high pressure superheated steam, which is passed through a condensing steam turbine coupled to an electric generator. Thus, through use of various streams for combustion and/or heat transfer, the thermal efficiency of the process may be greater than 60%. For example, the thermal efficiency of the process, based on the LHV of methanol product compared to total feed natural gas, may be greater than approximately 70% and can be above 75%.

In some implementations, at least a portion of the separated waste gas streams, which may include inert gases and carbon oxides, may be used as part of a fuel gas stream in a fired heater using as combustion air the gas turbine exhaust and/or an air stream. The heat generated may be used to preheat the hydrocarbon and steam feeds to the synthesis gas generation units. Since a significant quantity of argon and nitrogen, which may be from the oxygen stream and/or feed streams, may be included in the waste gas streams, a simple recycle of the $CH_4/Ar/N_2$ in streams back to the feed point of the synthesis gas generation system may cause a build-up of these components in the system. Thus, use of separated waste gas streams as fuel may reduce process waste streams and/or improve cost-efficiency of processes (e.g., due to the recycle as fuel).

Although the feed stream is described as including methane, the feed stream may include other components such as other hydrocarbons (e.g., ethane, propane, butane, pentane, benzene), other carbon and hydrogen containing compounds (e.g., carbon dioxide, carbon monoxide, hydrogen, alcohols, etc.), organic compounds, nitrogen, argon, etc. The feed stream may be natural gas, gases associated with the production of gasoline, combustible off-gasses from other processes, liquid hydrocarbons, etc. In some implementations, when the feed stream may be processed natural gas, for example, the sulfur compounds in natural gas may be removed or at least partially removed to prevent catalyst damage.

Although the synthesis gas is described as including carbon monoxide and hydrogen, the synthesis gas may also include other components, such as inert gases (e.g., nitrogen or argon). In some implementations, carbon oxides may include oxides of carbon, such as carbon monoxide and carbon dioxide. Although streams have been described to include various components in the implementations, the streams may include one or more other components.

Various other implementations may be utilized in combination with systems, such as system 400 illustrated in FIG. 1. In addition, various steps may be added, modified, and/or omitted. As an example, the carbon dioxide separated from the product synthesis gas stream may be provided to other processes (e.g., urea production processes or as a compressed stream for sequestration.). Alternatively, a portion of the separated $CO_2$ may be recycled back to the synthesis gas generation section and added to the feed gas to the POX, ATR, or EHTR.

Although the above illustration includes various streams being heated and/or compressed, other streams may be heated and/or compressed and/or shown streams may not be heated and/or compressed, as illustrated.

Although a specific implementation of the system is described above, various components may be added, deleted, and/or modified. In addition, the various temperatures and/or concentrations are described for exemplary purposes. Temperatures and/or concentrations may vary, as appropriate.

A number of implementations have been described. Nevertheless, it will be understood that various modifications may be made without departing from the spirit and scope of the implementations. Accordingly, other implementations are within the scope of this application.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a reactor" includes a combination of two or more reactors and reference to "a feedstock" includes different types of feedstocks.

What is claimed is:

1. A method for producing methanol, comprising;
producing oxygen in an air separation plant with air compressors driven by a gas turbine;
heating a hydrocarbon feed stream using exhaust from the gas turbine;
exothermically reacting a first portion of the heated hydrocarbon feed stream with at least one of steam or an oxidant gas comprising molecular oxygen to produce an exothermically generated syngas product;
endothermically reforming a second portion of the hydrocarbon feed stream with steam over a catalyst in a heat exchange reformer to produce an endothermically-reformed syngas product, wherein at least a portion of heat used in generation of the endothermically-reformed syngas product is obtained by recovering heat from the exothermically-generated syngas product and the endothermically reformed syngas product;

combining the exothermically generated syngas product and the endothermically-reformed syngas product to produce a combined syngas stream;

producing steam in a waste heat boiler by cooling the combined syngas stream, where the combined syngas stream leaving the waste heat boiler has a pressure from 70 bar to 100 bar;

separating water from the cooled combined syngas to produce a methanol plant feed at substantially reaction loop pressure and having less than about 2% $CH_4$ and less than about 0.2% $H_2O$;

after separating water, passing the cooled combined syngas to a methanol plant; and combining methanol plant combustible effluent with methane fuel to the gas turbine.

2. The method of claim 1, wherein the exothermically-generated syngas product is generated using a partial oxidation burner followed by a catalytic reforming section in a convectively heated steam plus hydrocarbon reformer.

3. The method of claim 1, wherein the hydrocarbon feed stream includes methane.

4. The method of claim 1, wherein the exothermically generated syngas product has a temperature greater than about 1000° C.

5. The method of claim 1, wherein the endothermic reforming occurs at a pressure of about 70 bars or greater.

6. The method of claim 1, further comprising producing substantially pure methanol using the cooled combined syngas at a rate of about 700 metric tons per day.

7. The method of claim 6, wherein the substantially pure methanol includes about 95% or greater methanol.

8. The method of claim 1, wherein the cooled combined syngas is passed to the methanol plant independent of using a feed stream compressor.

9. The method of claim 1, wherein the cooled combined syngas is passed to the methanol plant at a pressure in a range from about 70 to 100 bars.

10. The method of claim 1, wherein the second portion of the hydrocarbon feed stream includes a steam to active carbon ratio in a range of about 5 to 8.

11. The method of claim 1, wherein a gas-heated catalytic reformer (GHR) produces the endothermically-reformed syngas product by using catalyst filled tubes mounted in a vertical bundle with an inlet tube sheet at a top end and open bottom outlet ends.

* * * * *